United States Patent [19]

Love et al.

[11] 4,147,730
[45] Apr. 3, 1979

[54] SELECTIVE HYDROFORMYLATION PROCESS

[75] Inventors: Richard F. Love, Fishkill; Edwin R. Kerr, Wappingers Falls, both of N.Y.; John F. Knifton, Austin, Tex.

[73] Assignee: Texaco Inc., New York, N.Y.

[21] Appl. No.: 810,710

[22] Filed: Jun. 28, 1977

[51] Int. Cl.² ............................................. C07C 45/08
[52] U.S. Cl. .............................................. 260/604 HF
[58] Field of Search ...... 260/604 HF, 431 N, 632 HF

[56] References Cited

U.S. PATENT DOCUMENTS

| | | | |
|---|---|---|---|
| 3,450,730 | 6/1969 | Scheben et al. | 260/429 |
| 3,652,676 | 3/1972 | Kable et al. | 260/604 HF |
| 3,832,391 | 8/1974 | Parshall | 260/497 A |
| 3,981,925 | 9/1976 | Schwager et al. | 260/604 HF |
| 3,996,293 | 12/1976 | Knifton et al. | 260/604 HF |

*Primary Examiner*—Werren B. Lone
*Attorney, Agent, or Firm*—Thomas H. Whaley; Carl G. Ries; Bernard Marlowe

[57] ABSTRACT

This disclosure is concerned with the use of supported platinum halide, Group IVA metal halide catalysts suitable for the hydroformylation of α-olefin substrates to predominantly linear, straight-chain aldehydes.

11 Claims, No Drawings

SELECTIVE HYDROFORMYLATION PROCESS

SUMMARY OF THE INVENTION

This invention relates to the use of novel hybrid platinum catalysts suitable for the catalytic hydroformylation of α-olefin substrates to predominantly linear, terminally substituted aldehydes.

More specifically, this invention concerns the use of certain novel platinum halide, Group IVA metal halide catalyst complexes bonded or anchored to nitrogen-containing organic or inorganic supports which are useful in the selective hydroformylation of linear α-olefin to predominantly linear aldehydes under moderate conditions of temperature and pressure.

Hydroformylation, as used throughout this disclosure and claims refers to the process of preparing aldehydic products from linear α-olefins through the addition of carbon monoxide and hydrogen to the carbon-to-carbon unsaturated bond of said olefin substrate, in accordance with stoichiometry of equation (1), set forth below:

$$RCH=CH_2 + CO + H_2 \rightarrow RCH_2-CH_2-CHO \quad (1)$$

where R in this invention may be hydrogen or an alkyl, aryl, alkaryl, aralkyl or cycloalkyl group containing 1 to 28 carbon atoms.

BACKGROUND OF THE INVENTION

Over the past decade many highly active and selective catalysts for hydrocarbon reactions have been derived from transition-metal complexes. These homogeneous complex catalysts have several advantages over conventional heterogeneous catalysts in that the active centers are readily accessible and reactions involving their use characterized by a high degree of selectivity and reproducibility. However, the use of homogeneous catalysts on an industrial scale can lead to numerous practical problems, including corrosion, deposition of the catalyst on the reactor walls and recovery of the catalyst from reaction products. One way of overcoming these problems while retaining the advantages of the transition-metal complex catalyst is to attach the complex to the surface of a solid support. In particular, increased attention has been given recently to anchoring homogeneous transition metal catalysts to polymeric supports through the formation of one or more chemical bonds between the surface of the support and a ligand group involved in the metal complex. The transition-metal complexes may be attached to the surfaces of both organic and inorganic solids. Generally, these hybrid or "heterogenized" catalysts have certain intrinsic advantages over their homogeneous counterparts, particularly: (1) ease of separation from products, (2) enhanced size and positional selectivity, (3) ability to carry out sequential catalytic reactions and (4) ease of catalyst recycle. A number of research groups have, in recent years, demonstrated that a variety of transition-metal organometallic species possess excellent activity and selectivity for hydrogenation, isomerization and hydroformylation when bonded to macroreticular polymeric resins. However, olefinic hydroformylation studies have, to our knowledge, been carried out only with polymer anchored cobalt* and rhodium** catalyst complexes. The normal/iso aldehyde ratio with these catalysts is typically 1/3–3/1, hydroformylation being accompanied by concurrent isomerization of the unreacted olefin and reduction to alkanes.

*G. O. Evans et al, J. Organometal. Chem. 67, 295 (1974).
**See for example: K. G. Allum et al, J. Organometal. Chem., 87, 189 (1975): M. Capka et al, Tetrahedron Lett., 4787 (1971); and C. V. Pittman et al, J. Amer. Chem. Soc. 97, 1942 (1975).

In the broadest contemplated practice of this invention, aldehydes are produced from α-olefins substrates by the catalytically directed addition of hydrogen and carbon monoxide to said α-olefins in the presence of a catalytic quantity of a supported hydroformylation catalyst consisting of one or more platinum halides, in combination with one or more Group IVA metal halides (such as tin and germanium halides) bonded to nitrogen containing organic and or inorganic supports to form a reaction mixture, and heating the pressurized reaction mixture until substantial amounts of the desired aldehydes are produced.

In a narrower practice of this invention, aldehydic products containing from 3 to 31 carbon atoms are prepared by the catalytic addition of carbon monoxide and hydrogen to an α-olefin substrate containing from 2 to 30 carbon atoms by a process of:

(a) Admixing each mole of said α-olefin to be hydroformylated, in a deoxygenated reaction medium with at least a catalytic quantity of a supported hydroformylation catalyst consisting of one or more platinum halides, bonded to or anchored to one or more nitrogen containing organic and inorganic supports, to form a reaction mixture.

(b) Pressurizing said reaction mixture with at least sufficient carbon monoxide and hydrogen to satisfy the stoichiometry of the hydroformylation reaction described supra (Eq. 1);

(c) Heating said pressurized reaction mixture to temperatures of from about 20° to 130° C. until substantial formation of the predominantly linear alkyl aldehyde product is formed, and (d) Isolating said aldehyde products contained therein.

In a yet narrower embodiment of this invention, aldehydic products containing 3 to 31 carbon atoms are prepared by the catalytic addition of hydrogen and carbon monoxide to an alpha-olefin substrate containing 2 to 30 carbon atoms by the following steps:

(a) Mixing the catalyst, comprising an insoluble, macroreticular nitrogen-containing organic polymer or silica supported, amine-stabilized platinum-tin halide complex, containing a tin to platinum atomic ratio of 0.5 to 30:1, in a deoxygenated inert solvent and pretreating with carbon monoxide at 250 to 4000 psig for 15 to 90 minutes at temperatures of 20° to 90° centigrade, to form a pretreated reaction mixture.

(b) Dispersing the alpha-olefin, in the ratio of one mole per 0.001 to 0.1 mole of platinum catalyst used, then pressurizing to at least 250 psig with carbon monoxide and additional sufficient hydrogen to satisfy the stoichiometry of the hydroformylation reaction referred to above (Eq. 1), to form a pretreated reaction mixture.

(c) Heating said pressurized reaction mixture to temperatures of 20° to 130° centigrade until substantial formation of the aldehydic product is achieved, and (d) Isolating said aldehydic products contained therein.

In order to further aid in the understanding of this invention, the following additional disclosure is submitted:

A. Process Sequence and Variations

In general, the components of the hydroformylation reaction mixture, including optional inert solvent, olefin and catalyst may be added in any sequence as long as good agitation is employed to provide a good dispersion of the heterogeneous reaction mixture. For example, the following represent some variations insofar as the addition of catalyst components, inert solvents and olefin addition that may be made without departing from the inventive process. These modifications include:

(1) The catalyst may be preformed and added preformed to the reactor prior to the addition of the olefin and other inert solvent components.

(2) Preferably, to maximize the specific activity of said platinum catalyst, the catalyst is suspended in an inert solvent, under an inert atmosphere, prior to addition of the α-olefin substrate and the other components of the hydroformylation reaction mix.

(3) To minimize induction periods and to further maximize the specific activity of the supported platinum halide, tin(II) halide catalyst, a particularly preferred modification is that the suspension of said catalyst in an inert solvent is pretreated with superatmospheric pressures of carbon monoxide prior to the addition of the α-olefin substrate, and the other components of the hydroformylation reaction mix.

B. Supported Platinum Halide, Group IVA Metal Halide Catalyst

The catalysts of this invention consist essentially of platinum-tin halides complexed or anchored to five types of nitrogen-containing supports shown below:

(a) Polyvinylpyridine homopolymers derived from 4-vinylpyridine and 2-vinylpyridine (b) Vinylpyridine polymers crosslinked with divinylbenzene (c) Vinylpyridine-styrene-divinylbenzene terpolymers (d) Styrne based polymers having appended tertiary amine groups (e) Silica supports having chemically bonded to them organic nitrogen groups.

The supported platinum halide, Group IVA metal halide catalysts of this invention may be prepared by a number of methods. One convenient mode of preparation is to suspend the nitrogen-containing polymer or silica support in a suitable inert organic solvent or solvents used alone or with water. Illustrative of water-organic solvent mixtures are water-alkanol solutions. The procedure generally followed is to stir the polymer of silica support, the solvent or solvent mixture, Group IVA and platinum salt until the platinum is anchored to the polymer, or silica support. The platinum anchored-support or polymer is filtered and washed to resuspend said platinum support in a suitable inert solvent with the Group IVA halide salt.

Illustrative of suitable Group IVA metal halides which may be utilized in combination with a platinum halide to form an active hydroformylation catalyst are: tin(II) chloride, tin(II) bromide, tin(II) iodide, tin(IV) chloride and germanium(II) chloride. A preferred class of Group IVA metal halides to be used in the hydroformylation process of this invention are tin(II) halides selected from the group consisting of tin(II) chloride, tin(IV) chloride and tin(II) bromide.

The class of platinum halides which are utilizable in the presence of a Group IVA metal halide to form an active hydroformylation catalyst include platinum(II) bromide, potassium tetrachloroplatinate(II), potassium hexachloroplatinate(IV) and chloroplatinic acid.

The transition-metal catalysts of this invention are employed for the hydroformylation process when bonded to suitable macroreticular organic polymers are support. Illustrative of suitable organic polymer supports for this class of catalyst include poly-2-vinylpyridine, poly-4-vinylpyridine, 2-vinylpyridine-divinylbenzene copolymer, 4-vinylpyridine-divinylbenzene copolymer and vinylpyridine-styrene-divinylbenzene terpolymers. Also included are polystyrenes, styrene-divinylbenzene copolymers, polyethylenes, polypropylenes and styrene-butadiene polymers having attached or appended organic amine groups. The amine groups appended to the oganic polymeric supports useful in this invention may be directly bonded to the carbon chain of the polymer or they may be attached through a methylene group or groups. Furthermore, said appended amine may also possess alkyl radicals containing 1 to 12 carbon atoms or a cycloalkyl radical of 4 to 7 carbon atoms. A particularly preferred class of catalyst support consists of styrene-divinylbenzene copolymers with appended dimethylaminomethyl or pyrrolinylmethyl groups. A typical synthesis of such a support is illustrated in Example 8, below.

The transition metal catalysts of this invention are also employed for hydroformylation when bonded to silica which has organic amine containing groups chemically attached to it. Illustrative of suitable organic amines which can chemically be attached to dehydrated silica are hydroxypyridine, 2- and 4-methylolpyridine, beta-pyridinethanol, N,N-dimethylaminoethanol and dimethylaminomethylphenol. A particularly preferred catalyst support consists of 4-hydroxypyridine chemically attached to dehydrated silica through the formation of a pyridinoxy-silicon bond. Synthesis of such a transition metal complex of 4-hydroxypyridine bonded to silica is shown in Example 12, below. Other organic amines which can be chemically bonded to dry silica are those which also possess the trimethoxysilane moiety. Illustrative of this type amine are dimethylaminopropyltrimethoxysilane, 3-(2-aminoethylaminopropyl)-trimethoxysilane and 3-(4-pyridinyl)propyltrimethoxysilane. A typical synthesis of such a support is illustrated in Example 13, below.

Still another type of nitrogen containing silica support can be obtained by copolymerizing mixtures of vinylpyridines and vinyltriacetoxysilane and reacting the resultant copolymer with silica. A typical synthesis of such an amine-polymer coated silica is illustrated in Example 11.

C. Ratio of Stannous Chloride to Polymer-Ligand Stabilized Platinum Chloride in Supported Catalysts While any molar ratio greater than 0.1 mole of stannous chloride per mole of ligand-stabilized platinum chloride will produce active catalysts, the experimental work performed indicates that at least one mole of stannous chloride for each mole of platinum chloride is required for good catalyst activity, reproducibility and stability. The preferred ratio is from one to 2.5 moles of stannous chloride per mole of platinum chloride. Less than a 1:1 Sn/Pt ratio leads to poorer catalyst reproducibility and catalyst deactivation. Mole ratios appreciably greater than 2.5 to 1 of tin and platinum generally produce less active catalysts. Within the range of 1:1 to 2.5:1 Sn/Pt ratios, only moderate differences in catalyst activity and stability were observed. This preferred ratio is based upon the hydroformylation of hexene-1.

D. Ratio of Supported, Ligand Stabilized Platinum Catalyst to Olefin Substrate The quantity of catalyst employed in this process is normally not critical and a wide range of concentrations may be employed. In general, the process is desirably conducted in the presence of catalytically effective quantities of active platinum halide-Group IVA metal halide catalysts which yield the desired aldehydic product.

Molar ratios of 100 to 1500 moles of olefin per mole of platinum complex can be employed where alpha olefins such as hexene-1 are used as the substrate. Much lower ratios are not harmful but are economically unattractive. The favored mole ratio used for the examples in Tables I through IV were 200 to 500 moles of olefin per gram atom of platinum in the polymer or supported complex.

E. Olefins as Substrates

Alpha olefins ranging in carbon content from 2 to 30 carbon atoms can be employed as substrates for the hydroformylation reactions. Illustrative alpha olefins would be propene-1, butene-1, pentene-1, hexene-1, octene-1, nonene-1, decene-1, undecene-1, dodecene-1 as well as their higher homologues. Illustrative branched chain alpha olefins would be 4-methylpentene-1 and 3-methylpentene-1.

The olefins can be used as single discrete compounds, in the form of mixtures of olefins, with or without large quantities of saturated hydrocarbons.

F. Inert Solvent

The hydroformylation may be run in the presence of an inert diluent when operating in batch processes. Solvents such as methylisobutylketone, benzene, toluene, tetrahydrofuran, dimethoxyethane, and paraffins such as hexane, isooctane and cyclohexane. Highly polar solvents are not required but good solvents for the product aldehydes are best used.

G. Temperature Required for Hydroformulation

The temperature range which can be employed for the hydroformylation will depend upon the olefin employed, the total pressure, the mole ratio of hydrogen to carbon monoxide used, the concentration of reactants and the amount of catalyst and choice of support used for the platinum catalyst. Using hexane-1 as a typical alpha olefin and a 4-vinylpyridine-divinylbenzene copolymer as a ligand-support for a 2:1 mole ratio complex of tin/platinum chlorides, an operating temperature range is from 25° to 130° C. when using $H_2/CO$ mixtures having CO partial pressures of 250 psig or greater. Below 250 psig partial pressures of CO, the catalytically active platinum-tin complex deactivates and at temperatures above 130° C., decomposition of the polymeric support can occur. A preferred temperature range is 70° to 120° C. when the aforementioned olefin is hydroformylated at 1500 to 3500 psig of CO and $H_2$ using the catalyst system also described above.

H. Pressures Required for Hydroformylation

The pressures which can be employed for hydroformylation are variable and are dependent on the factors mentioned above. Using hexene-1 as a representative olefin and again, a 4-vinylpyridine-divinylbenzene copolymer as a ligand support for a 2:1 and 1:1 molar tin/platinum chlorides complex, an operable pressure range is from 500 to 4000 psig when a 1:1 mole ratio of $H_2$ to CO and temperatures of 25° to 130° C. are employed. Pressures of 1500 psig or greater are preferred when operating within the preferred temperature range of 70° to 120° C. in order to reduce reaction times.

I. Hydrogen to Carbon Monoxide Ratio

The $H_2/CO$ mole ratio may be varied over a range of from 10/1 to 1/10 when suitable temperatures and total pressures are employed. A preferred narrower range is from 2/1 to 1/2 of hydrogen and carbon monoxide. The effect of differing ratios on yields and selectivities to aldehydic products is shown in Examples 15 and 42 to 48 in Table IV.

J. Effect of Hydroformylation Conditions

As shown by Examples 39–41 in Table IV, reducing the total gas pressure from 3400 to 1700 psig (1:1 $CO/H_2$) occasioned a diminution in conversion and yields over an eighteen hour period but selectivity to linear heptaldehyde rose to 68 percent. In Example 45, operating at 120° C. and 2000 psig total pressure (2:1 $H_2/CO$), the hydroformylation rate was faster than Example 40 and selectivity to linear heptaldehyde was higher still. Reversing the hydrogen to carbon monoxide ratio to 1:2.5 slowed the rate of hydroformylation as shown in Examples 46 and 47, Table IV but again increased the selectivity to linear aldehyde. We conclude that generally slower hydroformylation rates associated with lower total pressures and particularly lower hydrogen partial pressures favor increased product linearity. The predominent side reactions were found to be hexene-1 isomerization to hexenes-2,3 and reduction to n-hexane.

K. Reaction Times Required

As previously indicated in the discussions of temperatures, pressures and effects of reaction conditions on the hydroformylation reaction, experimental variables are important in arriving at reaction times. Generally, substantial conversions (50% or higher) of the olefin to aldehyde can be accomplished within eight hours when operating at or above 90° C. and at or above 2000 psig total pressure and 1000 psig partial pressure of hydrogen and using a catalyst having a Sn/Pt atomic ratio between 1:1 and 2.5:1. Frequently, at 3000 to 3500 psig of 1:1 CO and $H_2$, the hydroformylation was more than 95% complete within 150 minutes of reaching the reaction temperature of 90° C.

L. Catalyst Recycle

Empirically selected catalysts with platinum-tin chloride complexes anchored to different classes of nitrogen containing supports are active for hydroformylation upon recycle one or more times with fresh hexene-1 charge. Evidental recycle capability of selected catalysts are found in Tables II and IV. Samples of active catalysts derived from vinylpyridine polymers, having 1:1 to 2:1 tin to platinum atomic ratios were recovered and reused repeatedly for hexene-1 hydroformylation with no evident loss in activity, heptaldehyde yields remaining 85-98% when hydroformylation conditions were held at 90° C. and about 3000 psig of 1:1 CO and $H_2$. A platinum-tin chloride complex anchored to silica silylized by reaction with 3-(2-aminoethyl)aminopropyltrimethoxysilane also showed continued activity upon recycle (Examples 25-28, Table II). This property is very desirable in a commercial process, reducing the frequency of catalyst regeneration and lowering operating costs.

M. By-Products

As far as can be determined, without limiting the invention thereby, hydroformylation of olefins, catalyzed by the supported ligand-stabilized platinum-tin chloride complexes, leads to the formation of only three minor classes of by-products. These are isomerized olefins, hydrogenated olefins and high boiling materials formed via condensation reactions of the initially produced aldehydes.

N. Identification Procedures

Where applicable, the aldehydic products of this invention are identified by one or more of the following analytical procedures - gas chromatography (gc) infrared, elemental and nuclear magnetic resonance analyses. Unless otherwise specified all percentages are by mole rather than weight or volume, and all temperatures are in centrigrade rather than fahrenheit.

O. Conversion

As defined herein, conversion is the efficiency in transforming the α-olefin substrate to non α-olefinic products. Conversion is expressed in mole percent, and is calculated by dividing the amount of α-olefin substrate consumed during hydroformylation by the amount of α-olefin originally charged, and multiplying the quotient by 100.

P. Selectivity

Selectivity as defined herein, represents the efficiency in catalyzing the desired hydroformylation reaction relative to other undesired reactions or lack of reaction. In this instance hydroformylation to paraffinic aldehyde is the desired conversion. Selectivity is expressed as a percentile, and is calculated by determining the amount of paraffinic aldehyde product formed, divided by the amount of olefin converted and multiplying the quotient obtained by 100.

Q. Product Linearity

Product linearity, as defined herein, is the efficiency in catalyzing the desired hydroformylation relative to other undesired hydroformylation reactions. When α-olefins are to be hydroformylated, hydroformylation to the linear paraffinic aldehyde is the desired conversion. Linearity is expressed as a percentile, and is calculated by determining the amount of linear aldehyde product formed, divided by the total amount of aldehyde products formed and multiplying the quotient obtained by 100.

Having described the inventive process in general terms, the following examples are submitted to supply specific and illustrative embodiments.

EXAMPLES 1 to 9

Preparation of Nitrogen Containing Polymeric Supports and Ligand-Stabilized Platinum-Tin Chloride Complexes

EXAMPLE 1. 4-Vinylpyridine-divinylbenzene copolymer

4-Vinylpyridine (98 grams), dinvinylbenzene (4 grams), 600 ml of water and 0.2 grams of Natrasol 250H were charged to a one-liter stainless steel autoclave reactor. Azobisisobutyronitrile (0.5 grams) was added, the reactor sealed and flushed with nitrogen and heated to 80° C. at 2500 RPM stirring. After three hours the reactor was cooled to 30° C., an additional 0.5 grams of the butyronitrile added and the reactor heated to 80° C. with stirring for another 20 hours.

The reactor was cooled and the contents removed by water washing. The white solids were then washed with methanol and water and dried over solid KOH. Obtained 91 grams (82% yield) of copolymer calculated 6% crosslinked.

Example 2. 4-Vinylpyridine-styrene-divinylbenzene terpolymer

Styrene (73 grams), 4-vinylpyridine (24 grams), 600 ml of water, divinylbenzene (4 grams), Natrasol 250H and azobisisobutyronitrile reacted as in Example 1. Obtained 88 grams of fine white solids, 3.3% nitrogen.

Example 3. 2-Vinylpyridine-styrene-divinylbenzene terpolymer

Styrene (73 grams), 2-vinylpyridine (24 grams), dinvinylbenzene (4 grams), Natrasol 250H (0.3 grams) and 600 ml of water were reacted as in Example 1. There were obtained 90 grams of white solids containing 3.4% nitrogen.

Example 4. 2-Vinylpyridine-styrene-dinvinylbenzene terpolymer

Styrene (40 grams), 2-vinylpyridine (40 grams), dinvinylbenzene (1.6 grams), Natrasol 250H (0.3 grams) and azobisisobutyronitrile in 600 ml of water were reacted as described previously. There were obtained 67 grams of terpolymer containing 6.7% nitrogen.

Example 5.2 -Vinylpyridine-dinvinylbenzene copolymer

2-Vinylpyridine (50 grams), divinylbenzene (2 grams), water (350 ml), Natrasol 250HH (0.1 gram) and azobisisobutyronitrile were reacted at 80° C. for 6 hours. The mixture was cooled and filtered and 39 grams of white polymer were obtained. After drying over solid KOH elemental analysis showed it contained 10.7% nitrogen.

EXAMPLE 6. Poly-4-vinylpyridine

4-Vinylpyridine (49 grams) and benzoylperoxide (0.5 grams) were refluxed in 300 ml of benzene solution with rapid stirring. The solid polymer which formed was collected and washed repeatedly with benzene and finally dissolved in methanol. The methanol was evaporated leaving 40 grams of a hard, brittle polymer which remained methanol soluble.

Example 7. Chloromethylation of a styrene-divinylbenzene copolymer

Gaseous hydrogen chloride was rapidly passed into a stirred mixture of 300 grams of paraformaldehyde and 350 ml of methanol maintained at 0°-5° C. When all the paraformaldehyde had dissolved, the product was separated from the lower methanol layer, dried over $CaCl_2$ and distilled. Refractionation afforded 210 grams of chloromethyl ether, b.p. 58°-60° C.

Styrene-(2%) divinylbenzene copolymer (25 grams, 20-200 mesh) was dispersed in 150 ml of the above chloromethyl ether and allowed to swell at ambient temperature. After the cautious addition of stannic chloride (8 grams) the mixture was refluxed one hour and the polymer removed by filtration, washed with aqueous dioxane containig 10% (V/V) of concentrated hydrochloric acid and repeatedly with methanol. Upon drying there was obtained 36 grams of polymer containing 19% chlorine.

Example 8. Preparation of a styrene-divinylbenzene copolymer having appended pyrrolinylmethyl groups.

A sample of the above product (20 grams, Example 7) was dispersed in diethyl ether containing 30 grams of pyrrolidone and the mixture stirred three days at ambient conditions. The polymer was then separated by filtration, washed repeated with methanol and dried. The product consisted of 23 grams of a free-flowing material containig 6.2% nitrogen.

EXAMPLES 9-13

Preparation of Platinum-Tin Complexes of Nitrogen Containing Polymers

Example 9. Polymer Complexes Obtained using Chloroplatinic Acid

A sample of 4-vinylpyridine-divinylbenzene copolymer (2.0 rams) was dispersed in 50 ml of water and allowed to soak two hours whereupon chloropatinic acid ($H_2PtCl_6$, 0.1 gram) was added and the mixture stirred 6–18 hours by which time all the yellow color of the platinic acid had been absorbed by the polymer. The mixture was filtered and the solids dried.

The resin containing the absorbed platinum was soaked two hours in dry tetrahydrofuran, 0.2 grams of anhhydrous $SnCl_2$ were added and the mixture stirred overnight. After filtering, the yellow to yellow-orange solids to 2.08 grams (4.0% Pt, 2.6% Sn, Sn/Pt 1).

Variations of the above procedures used 1 and 2 grams of polymer, 0.1 to 0.4 grams of $SnCl_2$ or 0.12 to 0.24 grams of $SnCl_2.H_2O$ per 0.1 gram of chloroplatinic acid.

Poly-4-vinylpyridine, in water-methanol solutions, was also reacted with $H_2PtCl_6$ to form the insoluble platinum salts which were subsequently reacted with stannous chloride as illustrated above.

As an example, 1.0 gram of poly-4-vinylpyridine gave 1.3 grams of resinous product containing 5.9% Pt and 5.8% Sn, Sn/Pt 1.6.

EXAMPLE 10. Polymer Complexes Obtained using Potassium Tetrachloroplatinite.

A 2.0 gram sample of a 4-vinylpyridine-dinvinylbenzene copolymer was stirred overnight in 75 ml of water containing 0.21 gram of $K_2PtCl_4$. The pale yellow solids were collected, dried and again dispersed in 35 ml of tetrahydrofuran containing 0.22 grams of $SnCl_2$.

Example 11. Preparation of a Vinylpyridine Ligand Attached to Silica

Vinyltriacetoxysilane (4.5 grams) and 4-vinylpyridine (19.7 grams) in 200 ml of benzene was treated with 0.2 gram of benzoyl peroxide and the solution heated under nitrogen to 80° C. with rapid stirring. After 35 minutes an additional 0.3 gram of peroxide was added and heating continued for 90 minutes by which time some gummy polymer began to form on the flask walls. Silica (20 grams, 240 mesh), wet with 1 ml of water was added to the above mixture and the reaction continued for an additional 3 hours. Xylene (200 ml) was then added to the stirred mixture and the benzene distilled off until a head temperature of 120° C. was reached.

After a further 5-hour reflux the mixture was filtered, the gummy solids collected and continuously extracted with methanol for 24 hours. The solids were removed and dried over KOH, to give 16.2 grams of solid containing 2.2% nitrogen.

Platinum-tin chloride complexes of the above support were prepared by the procedure outlined in Example 10, above.

Example 12. Preparation of a Platinum-Tin Chloride Complex of 4-Hydroxypyridine Sorbed on Silica 4-Hydroxypyridine (0.7 gram) dissolved in 50 ml of methanol was reacted with 0.1 gram of chloroplatinic acid. Silica (10 grams, 240 mesh) and 125 ml of xylene and the thick mixture rapidly stirred and heated. As the methanol distilled off, an additional 500 ml of xylene were slowly introduced, then removed by slow distillation. The semi-solid residue was then stripped to dryness at 100° C. and 15–20 mm of pressure.

The dry residue (10.2 grams) was added to a solution of 0.20 gram of stannous chloride in 130 ml of tetrahydrofuran, the mixture stirred overnight and the solids recovered by filtration. Obtained were 10.1 grams of catalyst containing 0.66% platinum, 0.95% tin and having a Pt/Sn of 2.36.

EXAMPLE 13

Preparation of a Platinum-Tin Complex of a Silylized Silica

Xylene (150 ml) containing silica (5 grams, 240 mesh) was refluxed for 30 minutes with provision for water take-off. 3(2-Aminoethylaminopropyl)trimethoxysilane was then added and the reflux continued for 3 more hours followed by slow distillative removal of most of the xylene. The residue was filtered, washed with benzene and after drying the solids were stirred overnight in a methanolic solution of chloroplatinic acid (0.1 gram). The platinum impregnated silica was separated, washed repeatedly with methanol and dried. It was then dispersed and stirred in tetrahydrofuran containing stannous chloride (0.2 gram) for 12 hours, separated by filtration, washed repeatedly with tetrahydrofuran and dried in vacuo. The dried catalyst amounted to 6.59 grams and contained 1.27% platinum and 0.81% tin (Sn/Pt molecular ratio 1.05).

EXAMPLES 14-52

Platinum Catalyst Evaluation

Hydroformylation studies were carried out in a one-liter Hastelloy autoclave equipped with a magnadrive stirrer, sampling valve and a $H_2CO/N_2$ gas supply. The reactor contained water cooling-steam coils and an electric heate with automatic controls to permit rapid heating and cooling as well as constant temperatures during runs. Stirring rates of 700 rpm were usually employed.

Platinum-tin catalyst (ca. 2 gm, containing 0.13–0.38 mg Pt) dispersed in solvent, usually benzene (ca. 200 ml) was pretreated for 45–60 minutes with CO at 250–3000 psig, the pressure released and hexen-1 (100 mmoles) and the CO and $H_2$ mixture charged to the desired pressure. The mixture was brought to temperature and maintaind at temperature with stirring for periods of 2 to 18 hours. Small (0.5 ml) samples were usually withdrawn at regular intervals and the extent of hydroformylation determined by GLC using a 10-ft. ¼-inch column of 7% loaded SE-30 on Chromasorb "G" or alternatively a 150-ft. 0.01-inch capillary column. Product identification was by IR, NMR and by comparison with authentic samples. After reaction, the autoclave was cooled, disassembled and the product aldehydes isolated by distillation in vacuo.

Recovered platinum catalyst in solvent (200 ml) was recycled to the autoclave reactor with fresh hexene (100 mmole) annd hydroformylation to heptaldehydes carried out as described above.

Platinum catalysts recovered from hydroformylation reactions were found to be relatively stable at ambient conditions and could be stored for dys in closed vessels without special precautions. Upon reuse, including pretreatment with superatmospheric pressure of CO as described above, no change or loss in catalyst activity was observed.

Table I

Hexane-1 Hydroformylation using Supported Platinum-Tin Chlorides Catalysts

| Example | Catalyst composition | mg atom Pt used | Sn/Pt ratio | Hexene-1 conversion | Aldehyde Selectivity | % Product Linearity | Isomerization to 2,3-hexenes | Reduction to hexane |
|---|---|---|---|---|---|---|---|---|
| 14 | 4-VP-(6%)DVB copolymer, Pt-tin chlorides complex | 0.51 | 1.1 | >99.8 | 90 | 54 | Trace | 4.6 |
| 15 | 4-VP-(6%)DVB copolymer Pt-Sn chlorides complex | 0.43 | 2 | 99 | 98 | 55 | — | 1 |
| 16 | 4-VP-(10%)DVB copolymer, Pt-ton chlorides complex | 0.07 | 1.4 | 86.5 | 74.2 | 61 | ND | ND |
| 17 | 4-VP-(13%)DVB copolymer, Pt-tin chlorides complex | 0.05 | 0.4 | 5 | 20 | 63 | — | Trace |
| 18 | 4-VP-(6%)DVB copolymer containing platinum chloride but no tin | 0.46 | Zero | 1 | None | — | — | <1 |
| 19 | Poly-4-vinylpyridine, Pt-tin chloride complex | 0.39 | 1.6 | 100 | 97.9 | 54 | — | 2.1 |
| 20 | 2-VP-(8%)DVB copolymer, Pt-tin chlorides complex | 0.45 | 1.9 | 52.4 | 78.8 | 68 | — | <1 |
| 21 | 2-VP-styrene(1:3 ratio)-DVB terpolymer, Pt-tin chlorides | 0.35 | 2 | 53.5 | 98 | 60 | ND | ND |
| 22 | Styrene-(2%)DVB copolymer with appended $CH_2NC_4H_8$ groups, Pt-tin chlorides complex | 0.48 | 2 | 30 | 4.3 | 60 | ND | ND |

All reactions conducted in a stirred Hastelloy reactor using 100 mmoles hexene-1 in 200 ml of benzene. Reaction conducted at 90° C. and 3000–3300 psig of 1:1 CO and $H_2$ for 8 hours. 4-VP is 4-vinylpyridine, 2-VP is 2-vinylpyridine, DVB is mixed divinylbenzene, ND is not determined.

Table II

Hexene-1-Hydroformylation with Silica Supported Platinum-Tin Chloride Catalysts[1]

| Example | Catalyst composition | mg atom Pt used | Sn/Pt ratio | Reaction time (hrs) | Hexene-1 conversion | Aldehyde Selectivity | Product linearity | Isomerization to 2,3-hexenes | Reduction to hexane |
|---|---|---|---|---|---|---|---|---|---|
| 23 | Pt-tin chloride complex of 4-hydroxypyridine on silica | 0.49 | 2 | 16 | 100 | 80 | 61 | 1 | 12 |
| 24 | Pt-tin chloride complex of 4-vinylpyridine-triacetoxy-vinyl silane copolymer reacted with silica | 0.27 | 0.6 | 16 | 5 | 12 | 56 | Undetermined | 2 |
| 25 | Pt-tin chloride complex of 3-(2-aminoethyl)amino-propyl-trimethoxysilane silylized silica | 0.425 | 2 | 8 | 100 | 87.4[a] | 55 | Undetermined | 2.4 |
| 26 | Recycled 25 | 0.37 | | 6 | 100 | 97 | 56 | Trace | Trace |
| 27 | Recycled 26[b] | 0.30 | | 8 | 26 | 96 | 57 | 1 | Trace |
| 28 | Recycle3d 27 | 0.18 | | 8 | 70 | 87 | 62 | 22 | |

[1]Reactions conducted in a stirred Hastelloy reactor using 100 mmoles of hexene-1 in 200 ml of benzene. Operating conditions were 3000–3300 psig of 1:1 CO and $H_2$ at 90° C.
[a]0.5% heptanols also formed
[b]Conducted at 70° C., 3200 psig of 1:1 CO and $H_2$.

Table III

Hexene-1 Hydroformylation using Polymer Supported Platinum-Tin Chloride Catalysts

| Example[1,2] | mg. atom Pt used[3] | Sn/Pt ratio | Reaction time (hrs) | Hexene-1 conversion | Aldehyde Selectivity | % Product linearity | Isomerization to 2,3-hexenes | Reduction to hexane |
|---|---|---|---|---|---|---|---|---|
| 29 (a) | 0.62 | 0.6 | 18 | 10 | 43 | 62 | 10 | 40 |
| 30 (a) | 0.43 | 1.05 | 18 | >99.8 | 86.2 | 59 | Trace | 2.5 |
| 14 (a) | 0.51 | 1.1 | 18 | >99.8 | 90 | 54 | Trace | 4.6 |
| 15 (a) | 0.43 | 2.0 | 18 | 99 | 97 | 55 | — | 1.0 |
| 31 (a) | 0.37 | 3.0 | 18 | 42.5 | 86.1 | 62 | 14 | Trace |
| 32 (b) | 0.49 | 0.6 | 8 | 64 | 67.1 | 61 | 4.5 | 3.3 |
| 33 (b) | 0.43 | 1.0 | 8 | 8.6 | 59.3 | 59 | 23 | Trace |
| 34 (a) (Recycle 27) | 0.40 | 1.0 | 8 | >99.8 | 98 | 55 | Trace | 1 |
| 35 (b) | 0.46 | 2.1 | 8 | >99.8 | 96.6 | 55 | Trace | 2.8 |

Table III-continued

Hexene-1 Hydroformylation using Polymer Supported Platinum-Tin Chloride Catalysts

| Example[1,2] | mg. atom Pt used[3] | Sn/Pt ratio | Reaction time (hrs) | Hexene-1 conversion | Aldehyde Selectivity | % Product linearity | Isomerization to 2,3-hexenes | Reduction to hexane |
|---|---|---|---|---|---|---|---|---|
| 36 (b) | 0.43 | 2.8 | 8 | 38 | 78.9 | 61 | | Trace |
| 37 (b) | 0.35 | 4.8 | 8 | 12 | 91.7 | 60 | | Trace |

[1]Catalysts were Pt-tin chloride complexes anchored to a 4-vinylpyridine-(6%)divinylbenzene copolymer.
[2]All reactions run in a stirred autoclave at 90° C. and 3100-3500 psig of 1:1 CO and $H_2$.
[3]Based upon analysis of fresh catalyst and quantity of resin used.
(a)Catalyst pretreated with CO at 3000 psig at ambient temperatures, pressure released then repressurized with CO and $H_2$.
(b)Catalyst pretreated with 250 psig of CO at 90° C., then pressured with CO/$H_2$ mixture.

Table IV

Hexene-1 Hydroformylation using Supported Platinum-Tin Chlorides Catalysts[1]

| Example | Catalyst composition | mg. atom Pt used[3] | Pressure, psig | $H_2$/CO ratio | Temp, °C. | Reaction time (hrs) | Hexene-1 conversion | Selectivity | % Product Linearity | Isomerization to 2,3 hexenes | Reduction to hexane |
|---|---|---|---|---|---|---|---|---|---|---|---|
| 14 | 4-VP-(6%)DVB copolymer,[2] Pt-tin chlorides complex Sn/Pt ratio: 1.1 | 0.51 | 3100 | 1 | 90 | 18 | >99.8 | 90 | 54 | 1 | 4.5 |
| 38 | Recovered from Example 14 | 0.5 | 3400 | 1 | 90 | 18 | 98 | 79.5 | 56 | 7 | 10 |
| 39 | Recovered from 32 | <0.5 | 3300 | 1 | 90 | 18 | 100 | 94 | 54 | 1 | — |
| 40 | Recovered from 33 | <0.45 | 1700 | 1 | 90 | 18 | 12 | 94.1 | 68 | <0.5 | — |
| 41 | Recovered from 34 | 0.42 | 3000 | 1 | 90 | 18 | 100 | 92.7 | 55 | 1 | 4 |
| 15 | 4-VP-(6%)DVB copolymer,[2] Pt-tin chlorides complex, Sn/Pt ratio: 2.0 | 0.43 | 3100 | 1 | 90 | 18 | 100 | 97 | 55 | Trace | 1 |
| 42 | Recovered from Example 15 | 0.41 | 3100 | 1 | 90 | 8 | 100 | 93 | 57 | 1.5 | 5 |
| 43 | Recovered from 36 | 0.33 | 3100 | 1 | 90 | 8 | 20 | 5 | 36 | ND | ND |
| 44 | Recovered from 37 | 0.30 | 3000 | 1 | 89 | 8 | 100 | 85.7 | 55 | Trace | 2.9 |
| 45 | Recovered from 38 | 0.26 | 2000 | 2 | 120 | 8 | 93 | 34.4 | 71 | 15.6 | 42.2 |
| 46 | Recovered from 39 | 0.20 | 3300 | 1 | 90 | 4 | 100 | 98 | 55 | Trace | 1.8 |
| 47 | Recovered from 40 | 0.195 | 3500 | 0.4 | 90 | 9 | 75 | 94.6 | 62 | ND | ND |
| 48 | Recovered from 41 | 0.175 | 3400 | 1 | 90 | 1.25 | 100 | 98 | 55 | Trace | 1.9 |
| 30 | 4-VP-(6%)DVB copolymer,[2] Pt-tin chlorides complex, Sn/Pt ratio: 1.05 | 0.43 | 3100 | 1 | 90 | 20 | 100 | 86.1 | 59 | Trace | 2.5 |
| 49 | Recovered from Example 24 | 0.41 | 3000 | 1 | 91 | 4.25 | 100 | 97 | 55 | Trace | 2.7 |
| 50 | Recovered from 43 | 0.33 | 3200 | 1 | 89 | 4.3 | 100 | 97 | 55 | Trace | 2.0 |
| 51 | Recovered from 44[4] | 0.30 | 3300 | 1 | 90 | 8 | 4 | 75 | — | — | Trace |
| 19 | Poly-4-vinylpyridine, Pt-tin chlorides complex, Sn/Pt ratio: 1.6 | 0.39 | 3200 | 1 | 91 | 8 | 100 | 97.9 | 54 | — | 2.1 |
| 52 | Recovered from Example 19 | 0.34 | 3200 | 1 | 90 | 4.1 | 100 | 98 | 54 | Trace | 1.8 |

[1]Reactions conducted in a stirred Hastelloy autoclave, 100 mmoles hexene-1 in 200 ml of benzene. Example 32 used 200 mmoles hexene-1. Catalysts pretreated with CO at 3000 psig, excpet in Example 37 wherein the recovered catalyst from Example 36 was heated to 90° C. under 50 psig of CO immediately prior to use.
[2]4-VP is 4-vinylpyridine, DVB is divinylbenzene, ND means not determined.
[3]Pt used is based upon analysis of fresh catalyst and weight of recycled catalyst charged.
[4]Hexene-2 was used as the olefin substrate, n-heptane used as solvent.

EXAMPLES 53 TO 56

The Hydroformylation of Various Olefin Substrates Using Supported Platinum Halide-Tin Halide Catalysts Samples of supported platinum chloride-tin chloride catalyst, bonded to nitrogen-containing polymers or amine sorbed or silylized silica, are prepared as described in Examples 9-13. Suspensions of said catalysts in benzene (200 ml) are then evaluated for hydroformylation activity substantially as described in Examples 14-52, except that in separate runs, the hexene-1 charge in substituted by ethylene, propylene, tetradecene-1,4-methylpentene-1, and dodecene-1. Hydroformylation is achieved in all cases, the major aldehydic products are listed in Table V, below:

TABLE V

| Olefin substrate | Major aldehydic products |
|---|---|
| Ethylene | n-Propionaldehyde |
| Propylene | n-Butyraldehyde and 2-methyl-propionaldehyde |
| Tetradecene-1 | n-Tetradecanal and 2-methyl-tetradecanal |
| 4-Methylpentene-1 | 5-Methylhexanal and 2,4-dimethyl-pentanal |

As the examples of this invention indicate, the subject invention is advantageous in several respects compared to the corresponding hydroformylation technology of prior art. For example, the novel supported platinum halide, Group IV metal halide catalysts of this invention can be employed to hydroformylate alpha-olefins to the corresponding aliphatic olefins in high yields, in most cases exceeding 90 mole percent, while competing reduction and aldehyde condensation reactions are kept to a minimum. In addition, the solid catalyst is stable to ambient conditions and atmospheric oxygen and may be treated and reused with no special precautions.

Finally, the invention is quite advantageous in that numerous substitutions, modifications and changes can be made without departing from the inventive concept. However, the scope of the subject invention can best be understood by examining the claims which follow, read in conjunction with the preceding specification.

What is claimed is:

1. A process for preparing predominantly linear, straight-chain aldehydes containing from 3 to 31 carbon atoms by the catalytic hydroformylation of alpha-olefins containing from 2 to 30 carbon atoms with carbon monoxide and hydrogen by the steps of:

A. Admixing each mole of alpha-olefin to be hydroformylated, in a deoxygenated reaction medium, with at least a catalytic quantity of a supported hydroformylation catalyst consisting of at least one platinum halide, combined with at least one Group IVA metal halide bonded to a nitrogen-containing organic or inorganic support selected from the group consisting of:
  (a) Polyvinyl homopolymers derived from 4-vinylpyridine and 2-vinylpyridine,
  (b) Vinylpyridine polymers cross-linked with divinylbenzene,
  (c) Vinylpyridine-styrene-divinylbenzene terpolymers,
  (d) Styrene based polymers having appended to them tertiary amine groups, and
  (e) Silica supports having organic nitrogen groups appended to said silica, to form a reaction mixture,
B. Pressurizing said reaction mixture with at least a sufficient carbon monoxide and hydrogen to satisfy the stoichiometry of the hydroformylation reaction;
C. Heating said pressurized reaction mixture to temperatures of from 20° to 130° C. until substantial formation of the aldehyde product is formed, and
D. Isolating said aldehyde products contained therein.

2. The process in claim 1 wherein the olefin to be hydroformylated is in the form of a mixture of 1-alkenes.

3. A process for preparing predominantly linear, straight-chain aldehydes containing from 3 to 31 carbon atoms by the catalytic hydroformylation of alpha-olefins containing from 2 to 30 carbon atoms with carbon monoxide and hydrogen by the steps of:

A. Admixing each mole of alpha-olefin to be hydroformylated in a deoxygenated reaction medium, with at least a catalytic quantity of a supported hydroformylation catalyst consisting of at least one platinum halide, combined with at least one Group IVA metal halie bonded to a support of dehydrated silica having organic amine containing groups chemically attached to it, said organic amines being selected from the group consisting of 4-hydroxypyridine, 2-methylolpyridine, 4-methylolpyridine, beta-pyridinethanol, N,N-dimethylaminoethanol, dimethylaminomethylphenol, dimethylaminopropyltrimethoxysilane, 3-(2-aminoethylaminopropyl)trimethoxysilane and 3-(4-pyridinyl)propyltrimethoxysilane, to form a reaction mixture,
B. Pressurizing said reaction mixture with at least sufficient carbon monoxide and hydrogen to satisfy the stoichiometry of the hydroformylation reaction;
C. Heating said pressurized reaction mixture to temperatures of from 20° to 130° C. until substantial formation of the aldehyde product is formed, and
D. Isolating said aldehyde products contained therein.

4. A process for preparing predominantly linear, straight-chain aldehydes containing from 3 to 31 carbon atoms by the catalytic hydroformylation of alpha-olefins containing from 2 to 30 carbon atoms with carbon monoxide and hydrogen by the steps of:

A. Admixing each mole of alpha-olefin to be hydroformylated, in a deoxygenatedreaction medium, with at least a catalytic quantity of a supported hydroformylation catalyst consisting of at least one platinum halide, combined with at least one Group IVA metal halide bonded to a nitrogen-containing organic polymeric support selected from the group consisting of poly-4-vinylpyridine, poly-2-vinylpyridine, 4-vinylpyridine-divinylpyridine copolymer, 2-vinylpyridine-divinylpyridine copolymer, 4-vinylpyridine-styrene-divinylbenzene terpolymer, 2-vinylpyridine-styrene-divinylbenzene terpolymer, styrenedivinylbenzene copolymer with appended pryyolinylmethyl groups, to form a reaction mixture;
B. Pressurizing said reaction mixture with at least sufficient carbon monoxide and hydrogen to satisfy the stoichiometry of the hydroformylation reaction;
C. Heating said pressurized reaction mixture to temperatures of from 20° to 130° C. until substantial formation of the aldehyde product is formed, and
D. Isolating said aldehyde products contained therein.

5. The process of claim 4 wherein the olefin to be hydroformylated is hexene-1.

6. The process of claim 4 wherein the olefin to be hydroformylated is propylene.

7. The process in claim 3 wherein the olefin to be hydroformylated is in the form of a mixture of 1-alkenes.

8. The process of claim 4 wherein the platinum halide is selected from the group of platinum halides consisting of platinum(II) chloride, platinum(II)-bromide, potassium tetrachloroplatinate(II), potassium hexachloroplatinate(IV), and chloroplatinic acid.

9. A catalytic hydroformylation process for preparing predominantly linear, straight-chain aldehydes containing from 3 to 31 carbon atoms by the catalytic hydroformylation of alpha-olefins containing from 2 to 30 carbon atoms with carbon monoxide and hydrogen by the steps of:

A. Mixing each mole of alpha-olefin tobe hydroformylated in a deoxygenated reaction medium, with at least a catalytic quantity of a recyclable catalyst consisting essentially of platinum chloride-tin chloride bonded to a 3-(2-aminoethyl) aminopropyltrimethoxy silane silylized silica, to form a reaction mixture,
B. Pressurizing said reaction mixture with a least sufficient carbon monoxide and hydrogen to satisfy the stoichiometry of the hydroformyation reaction;
C. Heating said pressurized reaction mixture to temperatures of from 20° to 130° C. until substantial formation of the aldehyde product is formed;
D. Isolating said aldehyde products contained therein, adding additional alpha-olefin and forming another reaction mixture.

10. A process for preparing predominantly linear, straight-chain aldehydes containing from 3 to 31 carbon atoms by the catalystic hydroformylation of alpha-olefins containing from 2 to 30 carbon atoms with carbon monoxide and hydrogen by the steps of:

A. Admixing each mole of alpha-olefin to be hydroformylated, in a deoxygenated reaction medium, with at least a catalytic quantity of a supported hydroformylation catalyst consisting of at least one platinum halide, combined with at least one Group IV$_A$ metal halide bonded to an inorganic support selected from the group consisting of silica supports having organic nitrogen groups appended to said silica, to form a reaction mixture, B. Pressurizing said reaction mixture with at least a sufficient carbon monoxide and hydrogen to satisfy the stoichiometry of the hydroformylation reaction;

C. Heating said pressurized reaction mixture to temperatures of from 20° to 130° C. until substantial formation of the aldehyde product is formed, and D. Isolating said aldehyde products contained therein.

11. A process for preparing predominantly linear, straight-chain aldehydes containing from 3 to 31 carbon atoms by hydroformylation, in the presence of a recyclable hydroformylation catalyst, of alpha-olefins containing from 2 to 30 carbon atoms with carbon monoxide and hydrogen by the steps of:

A. Admixing each mole of alpha-olefin to be hydroformylated, in a deoxygenated reaction medium, with at least a catalytic quantity of a supported hydroformylation catalyst consisting of at least one platinum halide, combined with at least one Group IVA metal halide bonded to a nitrogen-containing organic support selected from the group consisting of:

(a) 4-vinylpyridine-divinylbenzene copolymer
(b) 4-vinylpyridine-styrene-divinylbenzene terpolymer
(c) 2-vinylpyridine-styrene-divinylbenzene terpolymer
(d) 2-vinylpyridine-divinylbenzene copolymer
(e) poly-4-vinylpyridine
(f) chloromethylated styrene-divinylbenzene copolymer
(f) styrene-divinylbenzene copolymer having appended pyrrolimethyl groups;

B. Pressurizing said reaction mixture with at least sufficient carbon monoxide and hydrogen to satisfy the stoichiometry of the hydroformylation reaction;

C. Heating said pressurized reaction mixture to temperatures of from 20° to 130° C. until substantial formation of the aldehyde product is formed; and D. Isolating said aldehyde products contained therein.

* * * * *